(12) United States Patent
Warner et al.

(10) Patent No.: US 6,409,659 B1
(45) Date of Patent: Jun. 25, 2002

(54) METHOD AND APPARATUS FOR DISPLAYING PHYSIOLOGICAL PATIENT DATA

(75) Inventors: Robert A. Warner, Durham, NC (US); Kevin P. Jessup, West Bend, WI (US); Gardar T. Middleton, New Berlin, WI (US); Mark Palma, Hartford, WI (US); Hansdieter Moessner, Voerstetten (DE)

(73) Assignee: GE Medical Systems Information Technologies, Inc., Milwaukee, WI (US)

(*) Notice: Subject to any disclaimer, the term of this patent is extended or adjusted under 35 U.S.C. 154(b) by 0 days.

(21) Appl. No.: 09/186,310

(22) Filed: Nov. 4, 1998

(51) Int. Cl.[7] .............................. A61B 5/00; A61B 5/02
(52) U.S. Cl. ...................... 600/300; 600/508; 382/128
(58) Field of Search ................................. 600/300–301, 600/481–486, 500–515, 521–525, 509, 595, 308–309; 128/923, 900, 903–905, 920–925; 382/128

(56) References Cited

U.S. PATENT DOCUMENTS

| | | | | |
|---|---|---|---|---|
| 5,622,178 A | * | 4/1997 | Gilham ........................ | 600/300 |
| 5,830,150 A | * | 11/1998 | Palmer et al. ............... | 600/523 |
| 5,846,206 A | * | 12/1998 | Bader .......................... | 600/534 |
| 5,956,013 A | * | 9/1999 | Raj et al. ..................... | 345/134 |
| 5,967,994 A | * | 10/1999 | Wang .......................... | 600/508 |
| 6,001,060 A | * | 12/1999 | Churchill et al. ........... | 600/300 |

* cited by examiner

Primary Examiner—John P. Lacyk
Assistant Examiner—Michael Astorino
(74) Attorney, Agent, or Firm—Michael Best & Friedrich LLP

(57) ABSTRACT

A method and apparatus for acquiring and displaying physiological patient data wherein the amplitude of the data is represented in color.

19 Claims, 3 Drawing Sheets

(1 of 3 Drawing Sheet(s) Filed in Color)

METHOD AND APPARATUS FOR DISPLAYING PHYSIOLOGICAL PATIENT DATA

BACKGROUND OF THE INVENTION

The invention relates to a method and apparatus for displaying physiological patient data, and particularly, to a method and apparatus for displaying physiological patient data in a colorized waterfall format.

Medical patient monitors are typically employed by physicians and other health care providers to monitor the physiological data of patients in operating rooms, intensive care units and emergency rooms, and for conducting long-term trend monitoring such as Holter monitoring or stress testing.

An array of sensors (also commonly called transducers) are typically connected to the patient to acquire the various physiological data. These data are then displayed on the screen of a monitor either in graphical or numerical form. These data may also be recorded or displayed on analog or digital strip chart recorders, spreadsheets and plotting programs.

In prior patient monitoring systems, and particularly in Holter and stress testing systems, it was found to be advantageous to take a series of successive periods of physiological patient data and cascade the periods in a quasi-three-dimensional display format to render visually obvious the abnormalities attendant to certain physiological conditions. However, this kind of data presentation can become cluttered if too many waveform samples are displayed at any one time. Moreover, some users of the equipment find such a display presentation visually unappealing, notwithstanding the clinical importance of the display technique.

SUMMARY OF THE INVENTION

Accordingly, the invention provides a method of displaying physiological and/or pathological patient data (hereinafter, the terms "physiological data" or "physiological patient data" shall be broadly defined as including pathological data, or any other type of patient information that is capable of being displayed using the invention). The method includes acquiring the physiological patient data, storing the physiological patient data in a waveform array, and displaying the physiological patient data on a monitor having a first (for example an "X") coordinate axis, a second (for example a "Y") coordinate axis, and a color component. In one form of the invention, the step of displaying the physiological patient data includes dividing the waveform array into a series of successive waveforms such that each successive waveform is plotted at a successive Y coordinate, and dividing each waveform into a series of successive data points such that each data point is plotted at a successive X coordinate and assigned a color according to the amplitude of the data point. The waveform array may be physiological data that represents individual physiological cycles such as heart beats, or the waveform array may be data that has been aggregated in some fashion such as averaging or filtering, or reduction to median complex.

The invention also provides an apparatus for acquiring and displaying physiological patient data. The apparatus includes a sensor or a transducer for acquiring physiological patient data from a patient, a processor for receiving the physiological patient data and for generating a waveform display on a monitor having an X coordinate axis, a Y coordinate axis and a plurality of color pixels such that the physiological patient data is stored in a waveform array. The processor divides the waveform array into a series of successive waveforms, and assigns each successive waveform a respective Y coordinate. The processor also divides each waveform into a series of successive data points and assigns each data point a respective X coordinate. Next, the processor assigns a color (which may be a shade of gray in the case of a black and white monitor, or a variation in intensity in the case of a monochrome monitor) according to the amplitude of the data point and plots the data point on the display monitor so that the pixel at the respective X and Y coordinate is energized using that color.

It is an advantage of the invention to provide a method and apparatus of displaying amplitude differences of physiological patient data using a gray scale or color display presentation.

Other features and advantages of the invention are set forth in the following drawings, detailed description and claims.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

Figure 1:
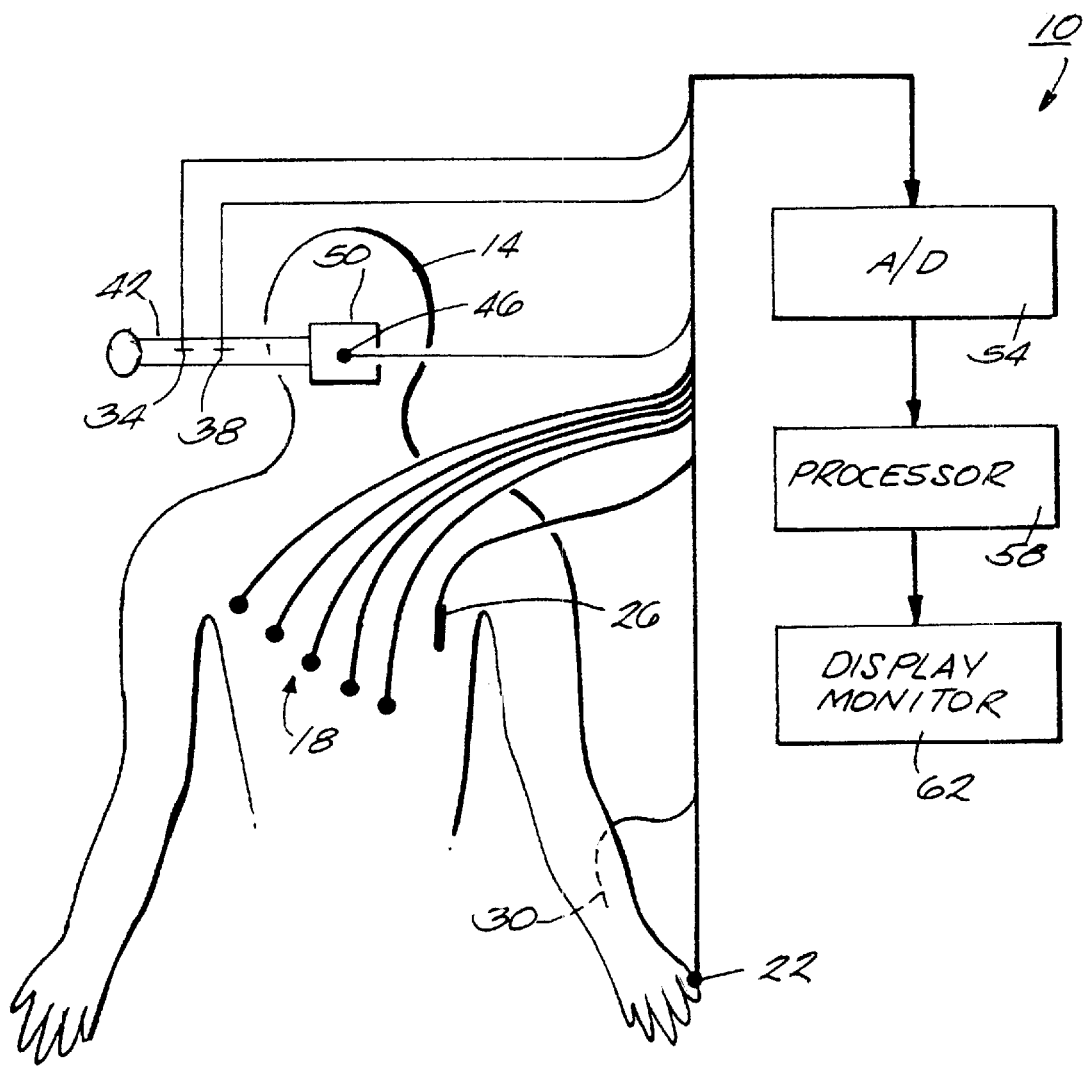
FIG. 1 is a block diagram illustrating a patient monitoring system according to the invention.

Before one embodiment of the invention is explained in detail, it is to be understood that the invention is not limited in its application to the details of the construction and the arrangements of the components set forth in the following description or illustrated in the drawings. The invention is capable of other embodiments and of being practiced or being carried out in various ways. Also, it is to be understood that the phraseology and terminology used herein is for the purpose of description and should not be regarded as limiting.

DETAILED DESCRIPTION OF THE PREFERRED EMBODIMENTS

FIG. 1 illustrates the patient monitoring system 10 of the invention. The patient monitoring system 10 acquires and displays physiological patient data. While the monitoring system 10 can be used in connection with any kind of clinical environment, in the preferred embodiment, the monitoring system 10 is for conducting long-term trend monitoring such as in Holter monitoring or stress testing. Monitoring system 10 is coupled to the patient 14 by an array of sensors or transducers which may include, for example, electrodes 18 mounted on the patient's chest for determining electrocardiogram and heart rate, an oximetry sensor 22 mounted on the patient's finger for measuring hemoglobin oxygen saturation, a catheter 26 for measuring hemoglobin oxygen saturation in the vena cava in the central venus pressure, an arterial canula 30 for measuring arterial systolic and diastolic pressures, flow meter 34 and a pressure sensor 38 in the endotrachial tube 42 for measuring trachial gas flow, and airway pressure, respectively, and sensors 46 in the patient's mask 50 for measuring the volume percentage of oxygen and $CO_2$ in the patient's mouth. Hereinafter, the terms "sensor" and "transducer" will be used synonymously, and each term will be defined as including the subject matter of the other term.

The signals derived from the sensors are converted from analog form to digital form by the analog to digital converter 54 and are then provided to a processor 58 that prepares the data for display on display monitor 62. The monitor is a conventional computer-style display monitor having a generally rectangular cathode ray tube or CRT (not shown). The CRT includes a plurality of pixels. The vertical location of the pixels is defined by a Y coordinate and the horizontal location is defined by an x coordinate. As is known in the art, each pixel is capable of being energized electronically so that the pixel emits light visible to the user of the monitoring system.

In the preferred form of the invention, the display monitor 12 is capable of displaying full color pixels, i.e., the display monitor is an RGB color monitor capable of displaying 256 colors or more. In other embodiments however, a black and white display capable of showing black, white and a plurality of gray shades (preferably no less than 64) in between is acceptable. The term "color" as used in this application is used to indicate either true color or shades of gray as described above unless the context indicates otherwise. Also, while any physiological patient data may be displayed in the format of the preferred embodiment, the invention will be discussed in the context of displaying long-term electrocardiogram ("ECG") data.

Figure 2:
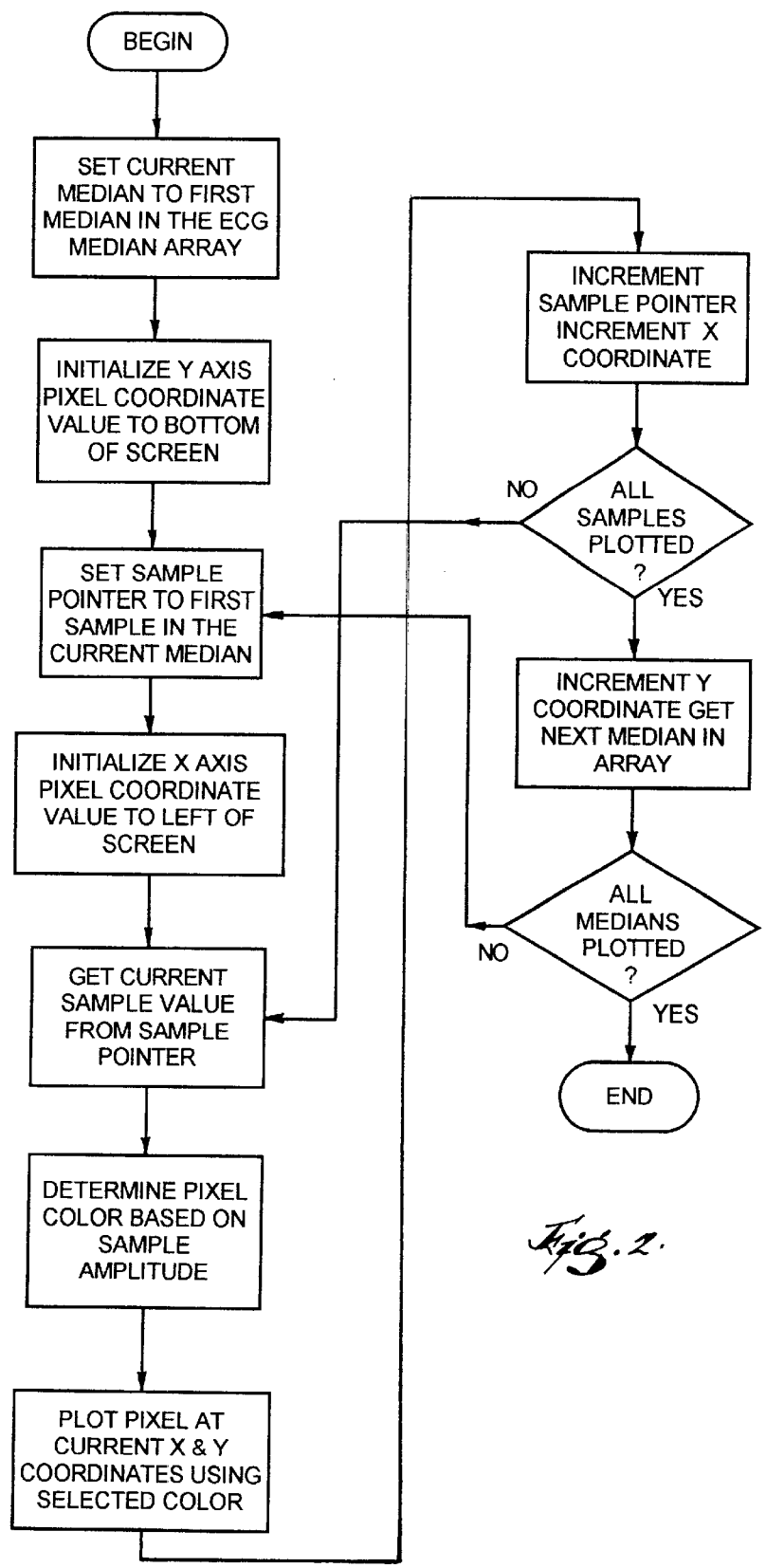
FIG. 2 is a flow chart illustrating the method of the invention.

FIG. 2 illustrates a flow chart of the process of the invention. The waveforms are stored in a waveform array. The processor sets the current waveform count to the first waveform in the waveform array. The processor then initializes the Y-axis pixel coordinate value to begin at the bottom of the CRT, sets the sample pointer to the first data sample in the current waveform and initializes the X-axis pixel coordinate value to begin at the left of the CRT. The processor then retrieves the current data point from the current waveform, determines a pixel color for the data point based on the amplitude of the waveform data point, and plots that data point at the respective X and Y coordinate using the selected color. In the preferred form of the invention, the color scheme of the monitoring system 10 is fully configurable. That is, the user can select any color to represent a given amplitude. Alternatively, the monitoring system 10 is programmed to provide the user with a set of manufacturer defined color schemes. In the preferred form of the invention, there would be graphical and numerical information generated on the display to indicate the corresponding voltage level of displacement for each color used.

The processor then increments the X coordinate and repeats the process for each data point in the current waveform until all data points in that waveform have been plotted. Once all data points in that waveform are plotted, then the processor increments the Y coordinate in order to retrieve the next waveform in the waveform array. This process is repeated until all of the waveforms in the waveform array are plotted. The results are displays such as those shown in FIG. 3.

Alternatively, the waveforms may be displayed by starting at the top of the screen and incrementing the Y coordinate downward for successive waveforms, or waveforms may be drawn by starting at an X and Y coordinate on the left side of the screen. First, an individual data point is plotted, then the processor increments the Y coordinate and the next data point is plotted until all data points for a waveform are plotted. Then, the X coordinate is incremented and the next waveform is plotted in the same manner.

Figure 3:
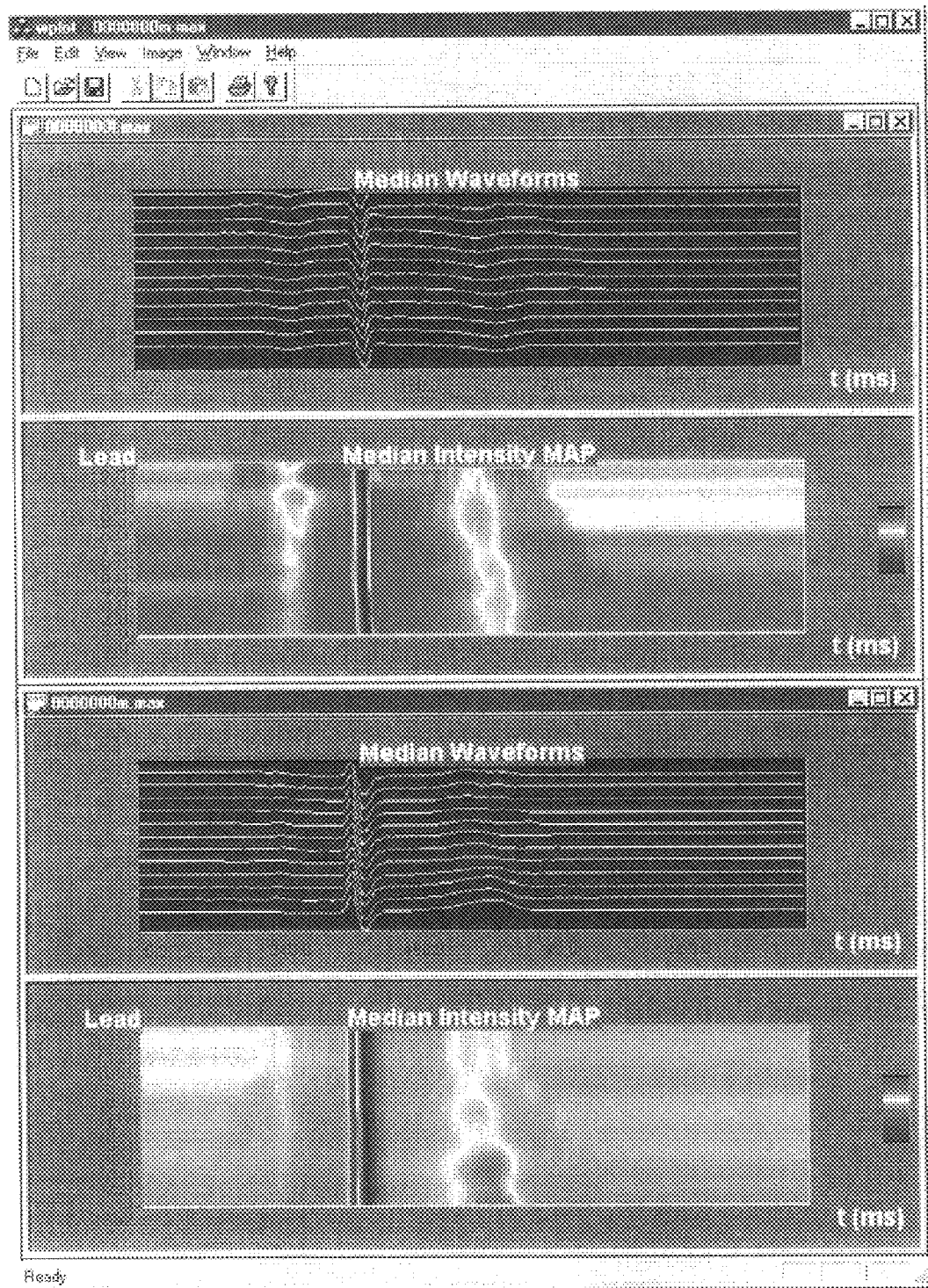
FIG. 3 is a color illustration showing a comparison of two waterfall displays of the prior art versus corresponding waterfall displays according to the invention.

FIG. 3 illustrates two waterfall displays of the prior art plotted above the same waveform data displayed using the method of the invention. The data labelled "Median Waveforms" in FIG. 3 is displayed so that the waveforms are stacked in a quasi-three-dimensional display presentation that allows some observation of long-term trends for a given set of physiological data. However, subtle trends that may exist in the data are difficult to observe. For example, in the uppermost Median Waveform of FIG. 3, there appears to be an amplitude shift in the waveform data just after 240 ms mark. It is difficult, however, to discern the meaning of this amplitude shift. The same waveform data is represented in FIG. 3 directly below the uppermost Median Waveform using the method of the invention and is labelled Median Intensity MAP. As shown in the uppermost Median Intensity MAP of FIG. 3, the long-term waveform amplitude shift is easily indicated by a change in color extending vertically at approximately the 240 ms mark. Moreover, variations in the amount of time between events (as shown on the X-axis) are also more easily detected. Again referring to the uppermost Median Waveform of FIG. 3, there is a slight change in amplitude that occurs between 480 ms and 720 ms. As shown in the corresponding Median Intensity MAP, the change in amplitude between waveform 1 and waveform 12, shifts to the left (i.e., from near the 720 ms mark in waveform 1 to nearer the 480 ms mark in waveforms 9, 10 and 11), thereby indicating a long-term shift in the timing of the event.

It is obvious from the contrasting views, that the physiological patient data colorized waterfall display is much more effective than the traditional prior art waterfall display in indicating subtle long-term trends and changes in physiological patient data.

Various other features and advantages of the invention are set forth in the following claims.

What is claimed is:

1. A method of displaying a physiological patient data waveform, to readily allow detection of changes in the waveform over time, the patient data waveform including physiological patient data having a plurality of data points, each data point representing an amplitude for the physiological patient data, said method comprising:
   a. acquiring the physiological patient data; and
   b. displaying the physiological patient data as at least one waveform on a monitor having an X coordinate axis and a Y coordinate axis, said displaying including assigning each data point a color corresponding to the amplitude of the data point.

2. A method as set forth in claim 1 wherein said physiological patient data is electrocardiogram data.

3. A method as set forth in claim 1, and further comprising storing the physiological patient data in a memory array.

4. A method as set forth in claim 1 wherein said memory array is a waveform array.

5. A method as set forth in claim 1 wherein said displaying includes dividing the physiological patient data waveform into a series of successive waveform segments.

6. A method as set forth in claim 5 wherein said displaying further includes plotting the waveform segments in side-by-side relation to allow detection of long term trends in the physiological patient data.

7. A method as set forth in claim 1 wherein said displaying further includes assigning an X coordinate and a Y coordinate to each data point and plotting each data point on the monitor at the respective X coordinate and the respective Y coordinate.

8. A method as set forth in claim 7 wherein the physiological patient data waveform is divided into a series of waveform segments and wherein said displaying further includes incrementing the X coordinate and the Y coordinate to plot the waveform segments in side-by-side relation.

9. A method of displaying a physiological patient data waveform, to readily allow detection of changes in the waveform over time, said method comprising:

a. acquiring the physiological patient data waveform;

b. storing the physiological patient data waveform in a memory array; and c. displaying the physiological patient data waveform on a color monitor having an X coordinate axis and a Y coordinate axis, said displaying including dividing the physiological patient data waveform into a series of successive waveform segments such that each successive waveform segment is plotted at a respective one of the X coordinate and the Y coordinate, dividing each waveform segment into a series of successive data points such that each data point is plotted at the respective other of the X coordinate and the Y coordinate, each successive data point having a discrete amplitude, and assigning a color according to the amplitude of the data point.

10. A method as set forth in claim 9 wherein the memory array is a waveform array.

11. A method as set forth in claim 9 wherein the physiological patient data waveform is electrocardiogram data.

12. A method of displaying physiological patient data, said method comprising:

a. acquiring the physiological patient data;

b. storing the physiological patient data in a waveform array, the waveform array including a series of waveforms, each waveform being divided into a series of data points having an amplitude;

c. providing a color display monitor having an X coordinate axis defining a series of X coordinates, a Y coordinate axis defining a series of Y coordinates, and a plurality of pixels corresponding to the X and Y coordinates;

d. setting the current waveform to the first waveform in the waveform array;

e. providing a Y coordinate counter and initializing the Y coordinate counter to zero;

f. providing an X coordinate counter and initializing the X coordinate counter to zero;

g. determining pixel color based on the amplitude of the data point;

h. plotting the current data point of the current waveform at the current X and Y coordinates in the color determined in (g);

i. incrementing the X coordinate counter and repeating (g) and (h) until all data points for the current waveform are plotted; and j. after all data points for the current waveform are plotted, incrementing the Y coordinate counter and repeating steps (f) through (i) until all waveforms in the waveform array are plotted.

13. An apparatus for displaying a physiological patient data waveform, to readily allow detection of changes in the waveform over time, the patient data waveform including physiological patient data having a plurality of data points, each data point having an amplitude representing the value of the physiological patient data, said apparatus comprising:

a display monitor having an X coordinate axis defining a series of X coordinates, a Y coordinate axis defining a series of Y coordinates, and a plurality of color pixels located at respective pairs of X and Y coordinates; and a processor for displaying said data points at respective pixels on said display monitor in colors corresponding to the amplitude of said data points, respectively.

14. An apparatus as set forth in claim 13, and further comprising a transducer for acquiring the physiological patient data from a patient.

15. An apparatus as set forth in claim 13 wherein said display monitor is a black and white display monitor capable of generating shades of gray in between black and white.

16. An apparatus as set forth in claim 13 wherein said display monitor is a red-green-blue color display monitor.

17. An apparatus as set forth in claim 13 wherein said apparatus is a Holter monitor.

18. An apparatus as set forth in claim 13 wherein said apparatus is a stress testing monitor.

19. An apparatus comprising:

a transducer for acquiring physiological patient data from a patient;

a display monitor having an X coordinate axis defining a series of X coordinates, a Y coordinate axis defining a series of Y coordinates, and a plurality of pixels corresponding to the X and Y coordinates, a processor for receiving the physiological patient data, for storing the physiological patient data in a memory array divided into a series of waveforms, and for generating a waveform display on said display monitor, such that each successive waveform is plotted at a successive Y coordinate on the monitor, and such that each waveform is divided into a series of successive data points, each data point being plotted at a successive X coordinate and being assigned a color corresponding to the amplitude of the data point so that the pixel corresponding to the X and Y coordinates is energized using the color assigned to the respective amplitude of the data point.

* * * * *